US012755833B2

(12) United States Patent
Shrum et al.

(10) Patent No.: US 12,755,833 B2
(45) Date of Patent: Oct. 6, 2026

(54) INTEGRATED COMPUTER BASED TOOLS AND TECHNIQUES FOR HEALTH AND DENTAL CARE PRACTICE MANAGEMENT

(71) Applicant: Virtual Front Desk, LLC, Naples, FL (US)

(72) Inventors: Lori A. Shrum, Belle Vernon, PA (US); John E. Tiano, Naples, FL (US)

(73) Assignee: Virtual Front Desk, LLC, Naples, FL (US)

( * ) Notice: Subject to any disclaimer, the term of this patent is extended or adjusted under 35 U.S.C. 154(b) by 0 days.

(21) Appl. No.: 18/220,876

(22) Filed: Jul. 12, 2023

(65) Prior Publication Data

US 2023/0352157 A1 Nov. 2, 2023

Related U.S. Application Data

(63) Continuation of application No. 16/858,935, filed on Apr. 27, 2020, now Pat. No. 11,791,037.

(Continued)

(51) Int. Cl.

| | |
|---|---|
| ***G16H 40/20*** | (2018.01) |
| ***G06N 20/00*** | (2019.01) |
| ***G06Q 10/10*** | (2023.01) |
| ***G06Q 30/016*** | (2023.01) |
| ***G10L 15/18*** | (2013.01) |
| ***H04M 3/493*** | (2006.01) |
| *G06Q 20/02* | (2012.01) |

(Continued)

(52) U.S. Cl.

CPC ............. *G16H 40/20* (2018.01); *G06N 20/00* (2019.01); *G06Q 10/10* (2013.01); *G06Q 30/016* (2013.01); *G10L 15/18* (2013.01); *H04M 3/493* (2013.01); *G06Q 20/027* (2013.01); *G10L 13/00* (2013.01); *G10L 15/26* (2013.01)

(58) Field of Classification Search

CPC ....... G10L 15/18; H04M 3/493; G06N 20/00; G16H 40/20

USPC .............................................................. 705/2

See application file for complete search history.

(56) References Cited

U.S. PATENT DOCUMENTS 9,824,188 B2 * 11/2017 Brown ................ G06F 3/04886
10,477,028 B1 * 11/2019 Tobin ...................... G06F 3/167

(Continued)

FOREIGN PATENT DOCUMENTS

CA 2397907 A1 * 7/2001 ............. G16H 40/67
CA 2397907 C * 3/2013 ............. G16H 40/67
WO WO-2020113506 A1 * 6/2020 ............. G16H 10/60

*Primary Examiner* — Jirapon Tulop

(74) *Attorney, Agent, or Firm* — IP Works Law

(57) ABSTRACT

A system (or architecture) for facilitating dental or other health care provider services, associated tasks and automated functionalities is provided as an integrated platform including an integrated combination of: a smart Interactive Voice Response (IVR) system, an automated front desk, a voice assisted integrated practice management system (PMS), automated billing and compliance, custom doctor portals, and automated reporting. The integrated platform is configured to provide a personal assistant who manages tasks and tracks patient records and/or is configured to limit or remove redundant software systems. The system includes or utilizes a Customer Relationship Management (CRM) system/software which is configured as the central hub of all information in and out of all interfaces or customer touch points.

11 Claims, 4 Drawing Sheets

Related U.S. Application Data

(60) Provisional application No. 62/839,432, filed on Apr. 26, 2019.

(51) Int. Cl.
*G10L 13/00* (2006.01)
*G10L 15/26* (2006.01)

(56) References Cited

U.S. PATENT DOCUMENTS

| | | | | |
|---|---|---|---|---|
| 2005/0261942 | A1* | 11/2005 | Wheeler | G16H 40/67 235/375 |
| 2010/0222649 | A1* | 9/2010 | Schoenberg | G16H 40/67 705/2 |
| 2019/0251417 | A1* | 8/2019 | Bennett | G06N 5/022 |
| 2019/0355447 | A1* | 11/2019 | Barkol | G16H 80/00 |
| 2021/0183505 | A1* | 6/2021 | Velaga | G06F 16/9535 |

* cited by examiner

INTEGRATED COMPUTER BASED TOOLS AND TECHNIQUES FOR HEALTH AND DENTAL CARE PRACTICE MANAGEMENT

CROSS-REFERENCE TO RELATED APPLICATIONS

This application claims the priority of U.S. Utility patent application Ser. No. 16/858,935, filed on Apr. 27, 2020 which claims priority to U.S. Provisional Application No. 62/839,432, entitled "INTEGRATED COMPUTER-BASED TOOLS AND TECHNIQUES FOR HEALTH AND DENTAL CARE PRACTICE MANAGEMENT" filed on Apr. 26, 2019, which is hereby incorporated by reference.

TECHNICAL FIELD

Various embodiments of the present invention generally relate to enhanced computer-based systems, processes, and techniques for managing and automating multiple aspects of the business systems of medical and dental practices.

INTRODUCTION

Health care practices and dental practices often spend tremendous amounts of personnel hours performing tasks that require human input and interactions. This is time that could be better spent servicing the clinical needs of patients. In a typical one-dentist, two-hygienist, two-assistant dental practice, up to eight front office people-hours per day might be spent on some combination of: confirming insurance coverage, phone usage, onboarding new patients, populating practice management software, documenting clinical notes of pertinent patient conversations, making/cancelling/rescheduling appointments, confirming upcoming appointments, dental laboratory interactions, communicating patient arrival to clinical staff, payment processing, insurance billing, patient billings, ordering prescriptions, and/or checking in patients, among many other tasks.

For example, a new patient call represents one of the most time-consuming procedures faced by the front desk staff. The first five to seven minutes of the call are used to gather information about the patient, such as name of patient, address, phone number, date of birth (Populate Practice Software—"PPS"); email address of patient or guardian; responsible party (RP) name, DOB, address, phone number, social security number (PPS); RP employer (PPS); and RP insurance company name, member ID, Group ID, phone number of insurance company (PPS). An appointment is then scheduled (PPS), and ending the call may include questions such as "Whom may we thank for referring you?" Other comments may be made to the caller such as: "We will be sending you an email with a link to our new patient forms" and perhaps an introduction to the practice, the doctor, the procedures that will be performed during that visit. Directions to the office may be necessary and time may be spent communicating that information to the patient. The staff member then may spend time calling or searching online for the responsible party's insurance company and their dental benefits. This process and the populating of the practice management system (PMS) typically takes 15-20 minutes. In total, from the time the team member picks up the phone until all of the above procedures and tasks are completed, up to 30 minutes of valuable time (or more) might be consumed.

It can be seen that the overall process of handling patient appointments, managing accounts and billing, insurance verification, registering new patients, preparing treatment plans, checking in with insurance companies on claims status, chasing after lost payments, and assisting doctors and other clinical staff during procedures can be time-consuming and inefficient. Compounding the problem is the fact that most software programs address just one or some of the tasks described above, and maintaining multiple software systems leads to higher operational costs. In addition, most systems and software applications do not integrate or communicate with each other, which leads to broken, unmanaged and inefficient systems.

DESCRIPTION

Various embodiments of the invention involve using a cloud-based technology solution for handling the time intensive tasks associated with the communication, check-in, onboarding, scheduling, confirming upcoming appointments, insurance management, billing, compliance, over the counter payment collection, and practice software field population of dental practice, for example, among many other tasks. The solution may employ artificial intelligence (AI) technologies that interface with practice management software as well as the phone system through an interactive voice response (IVR) architecture to which various tasks can be delegated. The solution embodies the vision of automating repetitive and mundane tasks of medical/dental/hospital/veterinary practices thereby decreasing staff expenses while increasing staff efficiency.

Various technologies and platforms may be used in the solution including Artificial Intelligence, System Generated Input, Interactive Voice Response, Customer Relationship Management (CRM) solutions/agents/systems/software, Voice Assistant (sometimes referred to herein as "DASH"), Smart Watch technologies, Kiosks, Insurance data base platforms and Cloud technologies. For example, the DASH voice assistant can be programmed to greet a caller, introduce itself by a name, disclose that the call will be recorded (and that this is not a person but a system), and then ask the caller to speak to DASH as it would a person. The system will then preform all of the tasks above without any office staff input unless requested by the caller.

Figure 1:
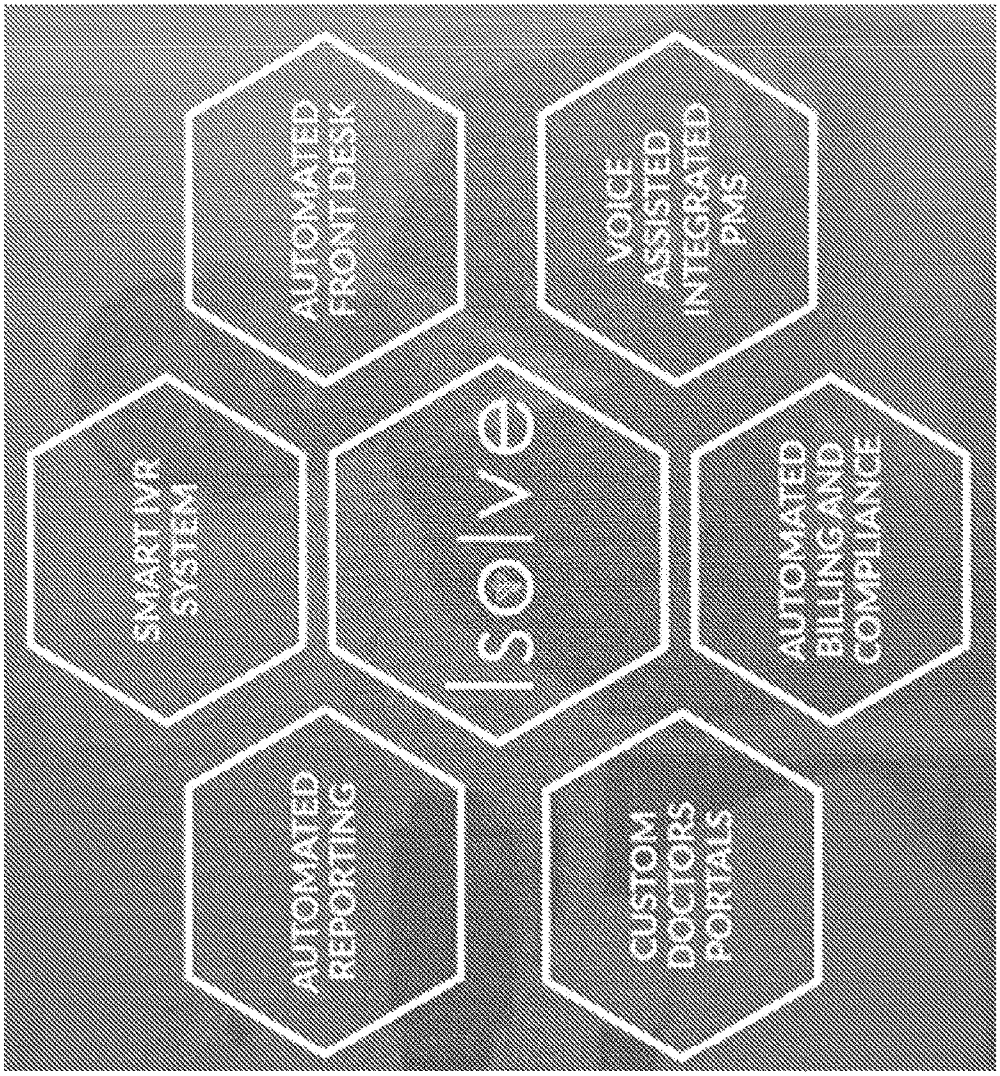
FIG. 1 is a diagram conceptually illustrating an example system including an integrated combination of: smart IVR system, automated front desk, voice assisted integrated practice management system (PMS), automated billing and compliance, custom doctor portals, and automated reporting.

In certain aspects of the invention, and with reference to FIG. 1, an "Isolve" platform can be configured to serve as an integrated platform to automate medical or dental front offices' front desk and related clinical activities. It can reduce or eliminate additional costs associated with needing to subscribe to or purchase multiple software applications. It also enables clinics to make more efficient use of their personnel and facilitates faster business growth. The Isolve platform embodies a system that manages data substantially seamlessly across different platforms and devices (e.g., any platform, framework or tool having a conversational interface). The system is convenient to access because it reduces the need for manual input and can automatically access and update patient details. The Isolve platform can provide a personal assistant who manages tasks and tracks patient records, while limiting the negative effects of human error. Isolve also embodies an integrated platform that limits or removes redundant software systems. As described below, one example of an Isolve system may include a combination of the following components: smart IVR system, automated front desk, voice assisted integrated practice management system (PMS), automated billing and compliance, custom doctor portals, and automated reporting, among others.

Figure 2:
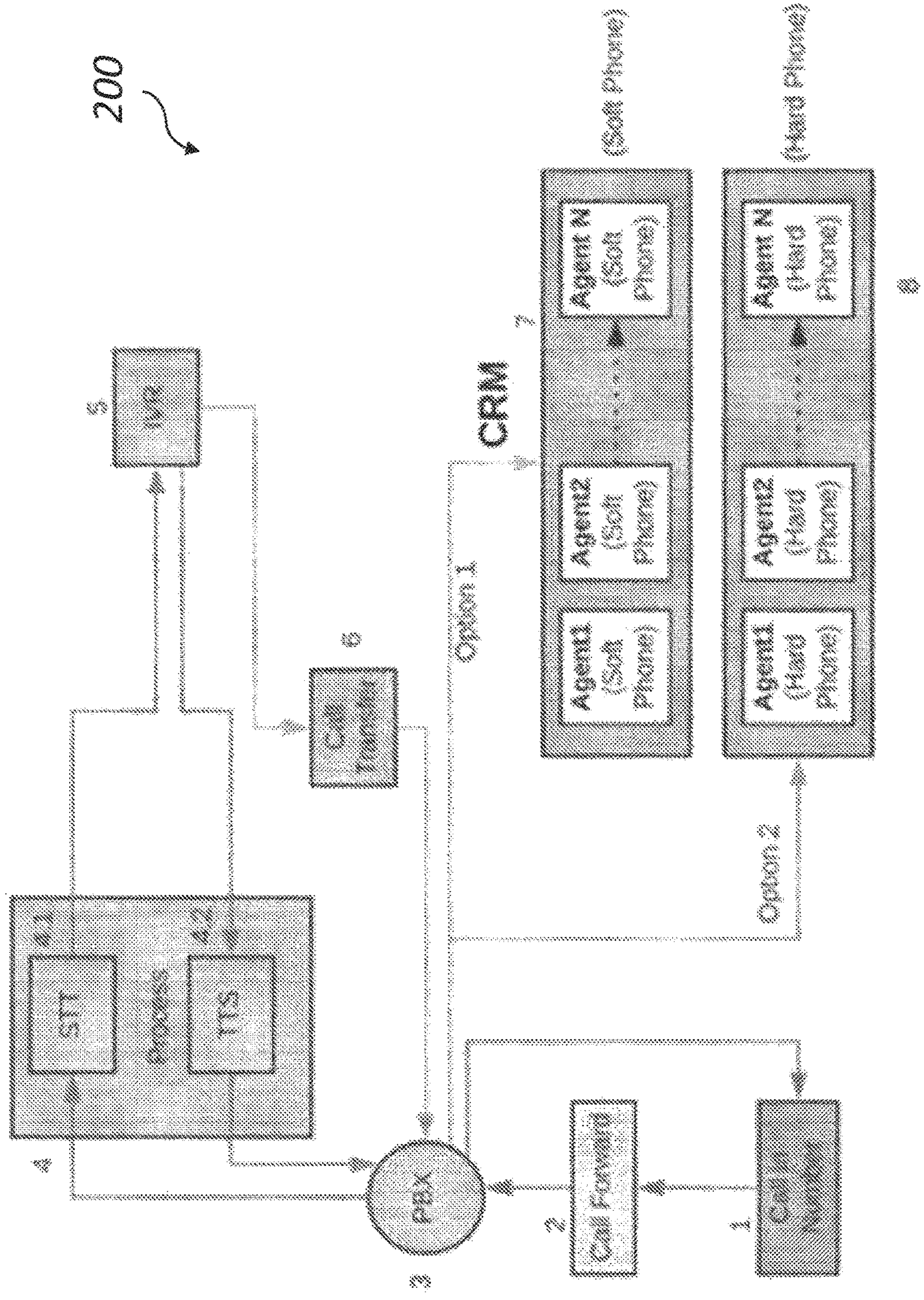
FIG. 2 is a diagram showing an example architecture and process flows which may be associated with a smart Interactive Voice Response (IVR) system structured in accordance with certain embodiments of the invention.

Referring to FIG. 2, a smart Interactive Voice Response (IVR) system 200 is structured and configured per the depicted example architecture and process flows inclusive of the descriptive notation set forth below (enumerated in reference to correspondingly numbered elements of the smart IVR system 200).

1. Existing Board number of the practice Ex: XXX-XXX•8000 (Number does not need to be ported.)
2. This is internal to Isolve, required to divert the call to invoke IVR.
3. PBX (Private Branch Exchange) handles
   i) incoming calls from Patients
   ii) Routing to different agents based on their availability (queuing).
4. Voice agent
   4.1. STT (Speech to Text)
   4.2. TTS (Text to Speech)
5. Dash (Contains All call Flows)
6. Transfer calls to agents via PBX.
7. CTI (computer telephony integration) integrated with CRM. In this option a soft VOIP phone can be used, providing the benefit of no telecom expenses. The agent will be able to see the call logs on CTI.
8. CTI integrated with CRM. In this case, the agent will be able to see the call details on the CTI, but the agent will receive the call on a physical phone.

SMART IVR SYSTEM. A pre-programmed voice assistant answers calls automatically. The patient can respond to the voice assistant just as he/she does with a normal human. The smart IVR listens to the voice input and takes the patient through the support process, and the IVR system can be made available on multiple simultaneously operating bases/channels/(agent) instances which are always or substantially always "on" and taking calls, for example, eight (8) 24×7×365 bases. The smart IVR can take multiple patient calls at the same time. The patient can easily set appointments and confirm booking without any wait time. FIG. 2 includes one example of a computer system architecture and certain process flows which may be associated with the smart IVR structured in accordance with certain embodiments of the invention.

AUTOMATED FRONT DESK. Patients who walk in with an appointment can check-in using a tablet at the front desk using their credentials. The doctor automatically gets notified on his smart watch or mobile phone (or another device) when the patient checks in to the clinic. Direct walk-in patient can enter credentials like name, date of birth, contact details, insurance details, etc., and schedule an appointment. The system automatically creates a patient profile which the patient can access at any time. The system automatically updates and tracks all the details on to the profile.

VOICE ASSISTED INTEGRATED PMS SYSTEM. A powerful helper who keeps everything running smoothly, so the office can focus on more important things. It is a voice assistant that enhances control and management of the practice with mainly voice commands. Treatment notes can be dictated to DASH so it can document them with voice notes. It communicates with the practice management system and updates the details for relevant patient's profile. DASH also facilitates management and tracking of tasks and appointments in real-time Doctors, dentists and other practitioners can automatically generate invoices for their patients once treatment is completed. The system automatically follows up with patients for any dues remaining through the IVR. The system automatically verifies insurance eligibility and updates the billing process. Patients can make payments at the front desk using tablet as once treatment has been completed.

CUSTOM DOCTOR PORTAL. Doctors can keep track of their appointments, their day-to-day tasks, and their patients' treatment progress on one application. Doctors have an option to manually add and make changes to their patients' treatment plans using their voices. The system then updates the progress on to the respective patient profiles. Doctors can access the portal from any device at any time.

AUTOMATED REPORTING. Practitioners can get automated reports about their practice on a weekly and monthly basis which can help them manage and improve their health care practices. The system generates reports related to the business, such as number of patients treated and new registered patients. Doctors and Dental Support Organizations (DSOs) can get (request, manually access and/or automatically receive) financial reports related to the revenue generated by the practice, total billings, payments collected and generated by the practice, and payments due on a monthly, quarterly or an annual basis.

Examples of various beneficial features of the system include: using AI to solve the business of professional practice; kiosk check-in; smart watch notification of patient arrival; smart watch interoffice communication; AI appointment scheduler; AI appointment confirmation; AI insurance verification and breakdown; AI auto population of practice management software; AI phone answering; morning huddle preparation; digital archive of all incoming and outgoing calls; AI lab tracking; AI report of all procedures performed that day as well as confirmation of insurance claim processing; voice assistant in every treatment room and front office work station; procedure "look ahead" alerts; task manager, electronic claims processing; chart note dictation and entry; in-operatory scheduling and payment: internal marketing options; social media option; online review management option; web site management option; and staff training module option, among many others.

Appendices 1-8 provide examples of how IVR systems and voice assistant systems can be implemented in accordance with various embodiments of the present invention. Further examples of different aspects of the invention, including examples of different computer system architectures and implementation details which may be applied to certain embodiments of the invention are provided below.

As previously discussed, there are problems with managing administrative tasks, front desk staff and other day to day business activities in the dental industry. Many existing processes such as patient registration, scheduling, recalling, marketing etc. are very manual and therefore inefficient.

Example embodiments and implementations described herein involve a multi platform approach that solves one or more, or particular combinations, of these problems. Dentistry can use this platform for all its clinics, and it is envisioned that the entire system (or portions thereof) can be packaged into an easily sellable product. In example embodiments, an IVR system is configured to have multiple flows each addressing a different request from a Patient/new patient ex: Billing questions, cancellation or changing existing appointment, emergency call etc. Each of the above mentioned call flows will have a breakout point to a front desk staff member. To facilitate this there needs to be an interface for the front desk person to be able to accept or reject a call and also have patient information along with the information he/she has already relayed to the IVR. (This can be achieved through leveraging a CRM that has call handling capabilities and will also act as a channel between different systems and databases.) In example embodiments and implementations, IVR is intelligent and powered by AI to allow for natural language processing (NLP) and responses.

In example embodiments and implementations, IVR is configured to be synced with a central database, Web portal, Kiosk application and any other front end and backend interfaces created now or in the future. The flows can be created where the scheduling is done by an actual person, and thus there will be a breakout from the IVR flow when the patient reaches that point in the process. In other embodiments, the IVR is configured to complete the scheduling through an intelligent automated system thereby allowing for an end to end call to be taken on by the IVR. In example embodiments and implementations, the IVR system is synced with a Text message and Email notification module, this system allows confirmations to be sent out to patients/doctors/admin automatically when new patients are added, new appointments scheduled or changed/canceled. In other embodiments, the IVR system is an inbound IVR system which accounts for incoming calls only, with the system potentially being upgradable to include/establish flows for outgoing calls ex: Recalling, Follow up calls, reminder calls etc.

In example embodiments and implementations, an IVR system can have single language (e.g., English or Spanish) or multi language capabilities. The IVR is configured to convert Speech to text for itself and the responses from the patient to document the flow of conversation and to make transcripts available to front end staff doctors/administrators for future reference or record keeping. The IVR is also configured to record and store all conversations in voice format. In example embodiments and implementations, the IVR is configured to facilitate/handle phone payments—Payment gateway integration. The IVR is configured to facilitate/handle insurance eligibility checks, co pay information—Insurance clearing house (3rd party integration). The IVR is configured to be able to read and write patient information, such as name, verification information, most recent visits, most frequently seen doctor or assigned doctor to the CRM and central database and further feed it into the practice management software. Example embodiments and implementations involve a package-able product configured to accommodate/work with different practice management softwares and different dental clinics of different sizes and processes, and includes or utilizes a central customer relationship management (CRM) system that houses all external integrations in and out of the system along with all data that is captured or fed through any of the input interfaces ex: telecom, website, Kiosk etc.

The Kiosk application, which can be a mobile or computer software application, is configured to provide a user interface that allows existing patients to check in when they arrive at the dental clinic. Preferably, the Kiosk is programmed/controlled to allow new patients to go through the entire signup process at the dental clinic in a very simple and intuitive manner. In example embodiments and implementations, the Kiosk application is configured/provided to include digital signature capability allowing patients to sign any HIPPA authorization forms or any other legal/compliance documents. The Kiosk can be configured to inform doctors & admin staff when a patient checks in at the practice. Preferably, the Kiosk application is configured/provided to allow new patients/existing patients to complete any part of the application they may not have completed over the phone or on the web and to allow patients to update their insurance information, or any other personal information at check in. In example embodiments and implementations, the Kiosk is configured to facilitate/process payments—Payment gateway integration. The Kiosk is configured to be able to verify patients insurance coverage and calculate co-pay—Insurance clearing house integration. In example embodiments and implementations, the Kiosk is connected to/interfaced with the CRM and through the CRM to the practice management software.

In example embodiments and implementations, the Kiosk application is configured to include or provide a Doctors portal that allows doctors to see patients as they check in at the front desk and includes/provide an interface for the doctor to see the patient's profile/records and be able to read and write to it Doctors portal is configured allow doctors to add treatment details and notes along with any future treatments that they believe the patient would need. Doctors portal can be linked to their calendar allowing them to see all of their existing and future appointments Doctors portal can be configured for example to allow doctors to schedule a future appointment with a patient if they have a consensus on the time and date while they are seeing him/her, thereby saving the patient the hassle of having to call in to schedule an appointment. (Patient can change the appointment to a different date/time later if needed by calling in or by using the web portal.) In example embodiments and implementations, all data from the doctors portal is fed into/interfaced with the CRM and through the CRM into the practice management software.

The Web portal is configured, for example, to allow patients to login and schedule a new appointment, change a previously made appointment to a different date/time, and see their patient profile along with a history or all previous treatment records and billing history. Preferably, Web portal is configured/controlled to allow new users to sign up (User authentication module) and create a new account and go through the new patient registration process online. Web portal can be configured to include/provide E-sign capabilities. In example embodiments and implementations, Web portal is configured to allow/facilitate online payments—Payment gateway integration. The web portal is configured to be able to verify insurance coverage and calculate copay-insurance clearing house integration. Preferably, the Web portal is configured/provided to allow users to complete any incomplete parts of their application on the portal that they might have carried on from the IVR or any other registration process (e.g., signing HIPPA authorization forms, or completing any other forms).

Figure 3:
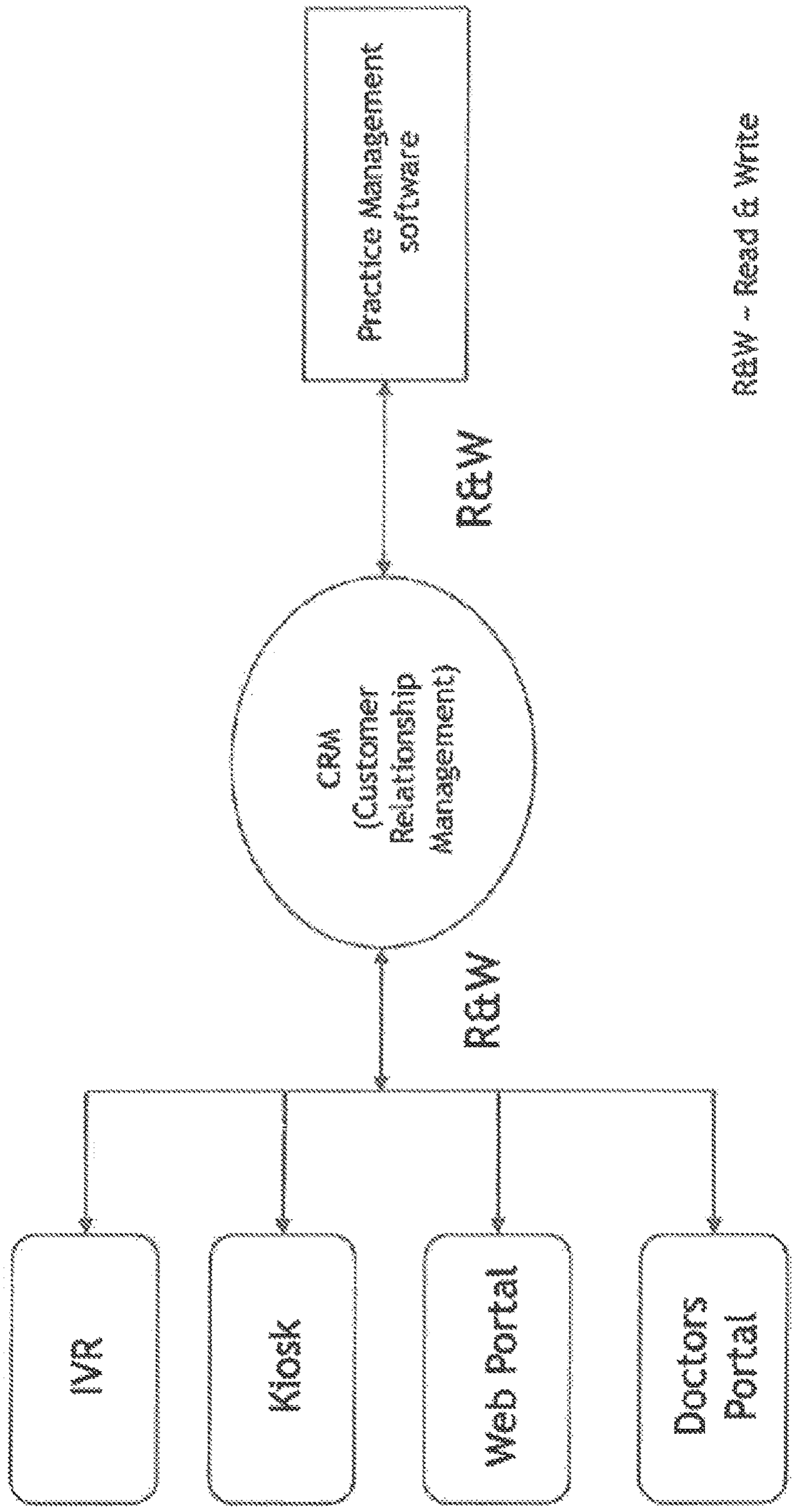
FIG. 3 is a diagram of an example high level solution in which a Customer Relationship Management (CRM) system/software is configured as the central hub of all information in and out of all interfaces or customer touch points.

In example embodiments, CRM (Customer Relationship Management) software, e.g., provided in the form of a customized application on the CRM, functions/serves as the central hub of all information in and out of all interfaces or customer touch points namely: IVR, Web Portal, Kiosk, Doctors Application. In example embodiments and implementations, CRM is configured/controlled to host all APIs. In example embodiments and implementations, CRM is configured/controlled to manage all telecom channels and switches. FIG. 3 is a diagram of an example high level solution in which a Customer Relationship Management (CRM) system/software is configured as the central hub of all information in and out of all interfaces or customer touch points.

Figure 4:
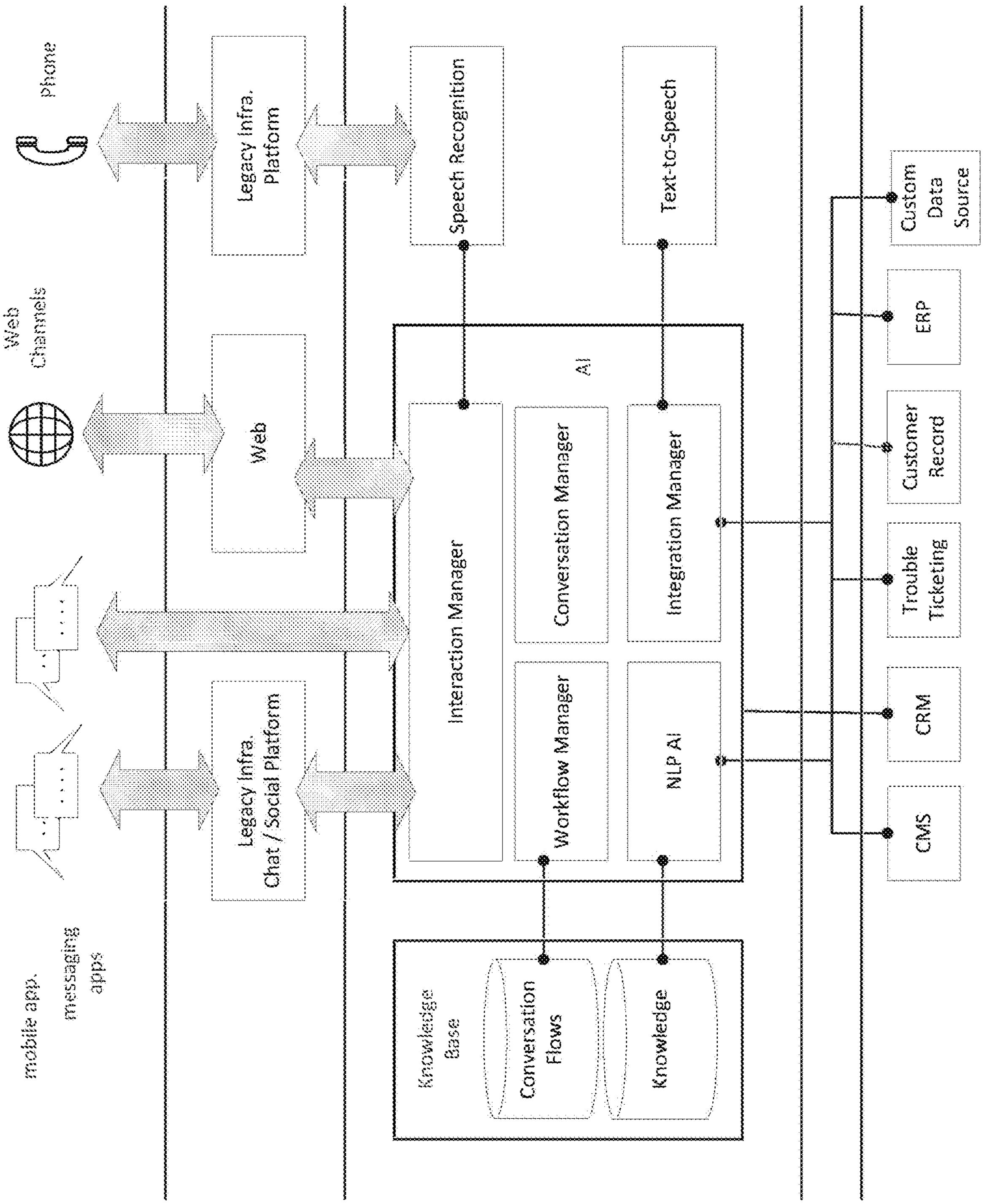
FIG. 4 is a diagram showing an example Interactive Voice Response (IVR) Architecture.

FIG. 4 is a diagram showing an example Interactive Voice Response (IVR) Architecture. In this example architecture, the IVR is configured (per the depicted example architecture, flows and operative interfaces) to utilize artificial intelligence (AI) to manage workflow, interactions with external devices/platforms, conversation, and integration with other systems/software/records/data sources. In example embodiments and implementations, the other systems/software/records/data sources include one or more of: a Trouble Ticketing module, a Customer Record (e.g., Patient Record), Enterprise resource planning (ERP) software, and a Custom Data Source Example systems/architectures leverage (include) an intelligent Rule-based IVR with NLP capabilities that facilitate and allow for a free flowing conversation between a user and a bot. In example embodiments and implementations, NLP is trained with a database of questions and answers and keywords thereby making it a specialized AI based NLP for the Dental industry. In other embodiments and implementations, a non rule based IVR powered by a well trained Neural network can be utilized.

Thus, in an example embodiment, a system for enhancing efficiencies in accessing and providing medical care includes an integrated combination of computer-based tools and interfaces including a plurality of interfaces and customer touch points and a Customer Relationship Management (CRM) software application configured to serve as a central hub of all information in and out of the plurality of interfaces and customer touch points. By way of example, the interfaces and customer touch points include: a smart Interactive Voice Response (IVR) system including a pre-programmed voice assistant configured to automatically answer calls and provide and control audible responses to caller inputs, a Web Portal configured to allow patients to login and schedule a new appointment, change a previously made appointment to a different date/time, and see their patient profile along with a history or all previous treatment records and a billing history, a Kiosk application configured to provide a user interface that allows patients to check in when they arrive, and to allow new patients/existing patients to complete any part of the application they may not have completed over the phone or on the web and to allow patients to update their insurance information, or any other personal information at check in, and a Doctors Application configured to be accessible via multiple different devices/interfaces at any time, to allow a doctor associated with a patient to manually add and make changes to treatment plans utilizing voice inputs and provide updates to patient profiles. In example embodiments and implementations, the CRM software application is configured/controlled to host all application program interfaces (APIs) of the system and/or to manage all telecom channels and switches of the system.

The IVR system is configured to be available on multiple simultaneously operating bases which are substantially always on and taking calls. The IVR can be provided by an intelligent Rule-based system architecture with natural language processing (NLP) capabilities that facilitate a free flowing conversation between a user and a bot. In example embodiments and implementations, the IVR is intelligent and powered by artificial intelligence (AI) to allow for natural language processing (NLP) and responses. The IVR can be configured to utilize artificial intelligence (AI) to manage workflow, interactions with external devices/platforms, conversation, and integration with other systems/software/records/data sources, e.g., including Enterprise resource planning (ERP) software.

The Web portal can be configured and integrated with a payment gateway to allow/facilitate online payments. The Web portal can be configured and integrated with an insurance clearing house to verify insurance coverage and calculate copay. The Web portal is configured/provided to allow users to complete any incomplete parts of an application or a form on the portal that the user had previously provided inputs to utilizing the IVR.

The Kiosk application can be configured and integrated with a payment gateway to allow/facilitate online payments. The Kiosk application can be configured and integrated with an insurance clearing house to verify insurance coverage and calculate copay.

Thus, in an example embodiment, a system for enhancing efficiencies in accessing and providing medical care includes an integrated combination of computer-based tools and interfaces including a plurality of interfaces and customer touch points including one or more of: a smart Interactive Voice Response (IVR) system including a pre-programmed voice assistant configured to automatically answer calls and provide and control audible responses to caller inputs, a Web Portal configured to allow patients to login and schedule a new appointment, change a previously made appointment to a different date/time, and see their patient profile along with a history or all previous treatment records and a billing history, a Kiosk application configured to provide a user interface that allows patients to check in when they arrive, and to allow new patients/existing patients to complete any part of the application they may not have completed over the phone or on the web and to allow patients to update their insurance information, or any other personal information at check in, and a Doctors Application configured to be accessible via multiple different devices/interfaces at any time, to allow a doctor associated with a patient to manually add and make changes to treatment plans utilizing voice inputs and provide updates to patient profiles. In example embodiments and implementations, the integrated combination of computer-based tools and interfaces includes a Customer Relationship Management (CRM) software application configured to serve as a central hub of all information in and out of the plurality of interfaces and customer touch points. In example embodiments and implementations, the CRM software application is configured to house all external integrations in and out of the system along with all data that is captured or fed through any of the interfaces and customer touch points, and the system is configured to and further feed the data into a practice management system (PMS).

Thus, in an example embodiment, an architecture for facilitating dental or other health care provider services, associated tasks and automated functionalities, the architecture includes an integrated platform including an integrated combination of: a smart Interactive Voice Response (IVR) system including a pre-programmed voice assistant configured to automatically answer calls and provide and control audible responses to caller inputs; an automated front desk including a front desk input interface (e.g., a tablet) configured to allow a patent to check in and to automatically generate and transmit a notification to a device informing a doctor and/or other medical personnel when the patient has checked in; a voice assisted integrated practice management system (PMS) configured to enhance control and management of practices of the dental or other health care provider primarily utilizing voice commands and to facilitate (automated) management and tracking of tasks and appointments in real-time, automated billing and compliance inclusive of automatically generating invoices for patients once treatment is completed and providing authorization forms or any other legal/compliance documents to patients; custom doctor portals configured to be accessible via multiple different devices/interfaces at any time, to allow a doctor associated with a patient to manually add and make changes to the treatment plans utilizing voice inputs and provide updates to patient profiles; and automated reporting to doctors and/or support organizations inclusive of providing reports related to the practice, numbers of patients treated and new registered patients, and financial reports related to revenue generated by the practice, total billings, payments collected and generated by the practice, and payments due on a monthly, quarterly or an annual basis. In example embodiments and implementations, the integrated platform is configured to provide a personal assistant who manages tasks and tracks patient records. In example embodiments and implementations, the integrated platform is configured to limit or remove redundant software systems.

Those skilled in the art will appreciate that embodiments of the invention described herein are intended to be structured and implemented for compliance with applicable local, state, and federal rules and regulations and good industry practices governing, among other things, HIPAA compliance, patient and patient record confidentiality, recorded telephone conversations, electronic transfer of personally identifiable information and sensitive patient data, information security and cybersecurity, "permission to speak to" rules and regulations, and other rules and regulations which govern health care related patient information storage, analysis and disclosure processes.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. For example, no particular aspect or aspects of the examples of system architectures, configurations, data definitions, or process flows described herein are necessarily intended to limit the scope of the invention, unless such aspects are specifically included in the claims.

Any element expressed herein as a means for performing a specified function is intended to encompass any way of performing that function including, for example, a combination of elements that performs that function. Furthermore, the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein.

In various embodiments, various models or platforms can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud computing techniques may be employed in connection with various embodiments of the invention.

Moreover, the processes associated with the present embodiments may be executed by programmable equipment, such as computers. Software or other sets of instructions that may be employed to cause programmable equipment to execute the processes may be stored in any storage device, such as a computer system (non-volatile) memory. Furthermore, some of the processes may be programmed when the computer system is manufactured or via a computer-readable memory storage medium.

It can also be appreciated that certain process aspects described herein may be performed using instructions stored on a computer-readable memory medium or media that direct a computer or computer system to perform process steps A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary. Memory and/or storage components may be implemented using any computer-readable media capable of storing data such as volatile or non-volatile memory, removable or non-removable memory, erasable or non-erasable memory, writeable or re-writeable memory, and so forth Examples of computer-readable storage media may include, without limitation, RAM, dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other type of media suitable for storing information.

A "computer," "computer system," "computing apparatus," "component," or "computer processor" may be, for example and without limitation, a processor, microcomputer, minicomputer, server, mainframe, laptop, personal data assistant (PDA), wireless e-mail device, smart phone, mobile phone, electronic tablet, cellular phone, pager, fax machine, scanner, or any other programmable device or computer apparatus configured to transmit, process, and/or receive data. Computer systems and computer-based devices disclosed herein may include memory and/or storage components for storing certain software applications used in obtaining, processing, and communicating information. It can be appreciated that such memory may be internal or external with respect to operation of the disclosed embodiments. In various embodiments, a "host," "engine," "loader," "filter," "platform," or"component" may include various computers or computer systems, or may include a reasonable combination of software, firmware, and/or hardware. In certain embodiments, a "module" may include software, firmware, hardware, or any reasonable combination thereof.

In various embodiments of the present invention, a single component may be replaced by multiple components, and multiple components may be replaced by a single component, to perform a given function or functions. Any of the servers described herein, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described hereinabove may be implemented in computer software using any suitable computer programming language such as .NET or HTML using, for example, conventional or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high-level languages include Ada, BASIC, C, C++, C#, COBOL, Fortran, Java, Lisp, Pascal, Object Pascal; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, power line communication or G.hn. Wireless communications described herein may be conducted with Wi-Fi and Bluetooth enabled networks and devices, among other types of suitable wireless communication protocols. The computer networks may also be embodied as one or more of the following types of networks: local area network (LAN); metropolitan area network (MAN); wide area network (WAN), virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the wireless device to the network. The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods and systems described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity. As applied herein, an extranet may include a network or internetwork generally limited to a primary organization or entity, but which also has limited connections to the networks of one or more other trusted organizations or entities (e.g., patients of an entity may be given access an intranet of the entity thereby creating an extranet).

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs); remote bridges can be used to create a wide area network (WAN) link between LANs, and/or, wireless bridges can be used to connect LANs and/or to connect remote stations to LANs.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to handle simultaneous execution of multiple computer programs.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a processor or application specific processor.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. Discrete components and features may be readily separated from or combined with the features of any of the other several aspects without departing from the scope of the present disclosure. Any recited method can be carried out in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

Certain embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It will be appreciated that those skilled in the art will be able to devise various arrangements which, although not explicitly described or shown herein, embody the principles of the present disclosure and are comprised within the scope thereof. Furthermore, all examples and conditional language recited herein are principally intended to aid the reader in understanding the principles described in the present disclosure and the concepts contributed to furthering the art, and are to be construed as being without limitation to such specifically recited examples and conditions. Moreover, all statements herein reciting principles, aspects, and embodiments as well as specific examples thereof, are intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

Although various systems described herein may be embodied in software or code executed by hardware as discussed above, as an alternative the same may also be embodied in dedicated hardware or a combination of software/hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc.

The flow charts and methods described herein show the functionality and operation of various implementations. If embodied in software, each block, step, or action may represent a module, segment, or portion of code that comprises program instructions to implement the specified logical functions. The program instructions may be embodied in the form of source code that comprises human-readable statements written in a programming language or machine code that comprises numerical instructions recognizable by a suitable execution system such as a processing component in a computer system. If embodied in hardware, each block may represent a circuit or a number of interconnected circuits to implement the specified logical functions.

Reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment. The terms "a" and "an" and "the" and similar referents used in the context of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as" or "for example") provided herein is intended merely to better illuminate the disclosed embodiments and does not pose a limitation on the scope otherwise claimed. No language in the specification should be construed as indicating any non-claimed element essential to the practice of the claimed subject matter. It is further noted that the claims may be drafted to exclude any optional element. As such, this statement is intended to serve as antecedent basis for use of such exclusive terminology as solely, only and the like in connection with the recitation of claim elements, or use of a negative limitation.

Groupings of alternative elements or embodiments disclosed herein are not to be construed as limitations. Each group member may be referred to and claimed individually or in any combination with other members of the group or other elements found herein. It is anticipated that one or more members of a group may be comprised in, or deleted from, a group for reasons of convenience and/or patentability.

While various embodiments of the invention have been described herein, it should be apparent, however, that various modifications, alterations and adaptations to those embodiments may occur to persons skilled in the art with the attainment of some or all of the advantages of the present invention. The disclosed embodiments are therefore intended to include all such modifications, alterations and adaptations without departing from the scope and spirit of the present invention as described herein.

The invention claimed is:

1. A medical practice management system, operating in a memory, incorporated for and within a single professional practice, the medical practice management system comprising:

a central management unit;

a kiosk communicatively coupled to the central management unit, the kiosk configured to be located at a physical location of the single professional practice; and an interactive voice unit communicatively coupled to the central management unit with the interactive voice unit performing natural language processing;

wherein:

the interactive voice unit accepts phone calls from a patient and generates natural conversations with each patient response being analyzed using an artificial intelligence unit trained on a plurality of conversations in a specific medical discipline to generate at least one new question to present to the patient based on a complete spoken response of the patient to a prior question and a determined intent of the complete spoken response of the patient, the central management unit performs at least one task based on information gathered by the interactive voice unit, and when the patient is at the physical location of the single professional practice, the kiosk is configured to interface locally with the patient.

2. The medical practice management system of claim 1, wherein the at least one task is scheduling an appointment with the patient and a doctor.

3. The medical practice management system of claim 2, wherein the central management unit sends appointment reminders and receives appointment confirmations from the patient.

4. The medical practice management system of claim 2, wherein the central management unit allows the patient to reschedule appointments with the doctor.

5. The medical practice management system of claim 1, wherein records related to the patient are stored, updated and distributed from the central management unit.

6. The medical practice management system of claim 5, wherein the central management unit is configured to allow a doctor to view, add, amend, and delete patient records.

7. The medical practice management system of claim 6, wherein the kiosk gathers information from the patient that is used to update the patient's record.

8. The medical practice management of claim 1, wherein central management system analyzes information gathered from the patient to customize and personalize the responses given to the patient.

9. A medical practice management system, operating in a memory, incorporated for and within a single professional practice, the medical practice management system comprising:

a central management unit;

a kiosk communicatively coupled to the central management unit, the kiosk configured to be located at a physical location of the single professional practice; and an interactive voice unit communicatively coupled to the central management unit with the interactive voice unit performing natural language processing;

wherein:

the interactive voice unit accepts phone calls from a patient and generates natural conversations with each patient response being analyzed using an artificial intelligence unit trained on a plurality of conversations in a specific medical discipline to generate at least one new question to present to the patient based on a complete spoken response of the patient to a prior question and a determined intent of the complete spoken response of the patient, the central management unit performs at least one task based on information gathered by the interactive voice unit, records related to the patient are stored, updated and distributed from the central management unit, the central management unit is configured to allow a doctor to view, add, amend, and delete patient records, and when the patient is at the physical location of the single professional practice, the kiosk is configured to interface locally with the patient.

10. The medical practice management system of claim 1, wherein the medical practice management system is configured to interface with at least one additional software system utilized by the single professional practice.

11. The medical practice management system of claim 9, wherein the medical practice management system is configured to interface with at least one additional software system utilized by the single professional practice.

* * * * *